United States Patent [19]

Polovina

[11] Patent Number: 5,759,764
[45] Date of Patent: *Jun. 2, 1998

[54] CRYOPRESERVATION SOLUTION

[75] Inventor: Milo R. Polovina, Wayzata, Minn.

[73] Assignee: Celox Laboratories, Inc., St. Paul, Minn.

[*] Notice: The term of this patent shall not extend beyond the expiration date of Pat. No. 5,580,714.

[21] Appl. No.: 658,666

[22] Filed: May 31, 1996

Related U.S. Application Data

[63] Continuation of Ser. No. 399,077, Mar. 8, 1995, Pat. No. 5,580,714.

[51] Int. Cl.$^6$ .............................. A01N 1/02; C12Q 1/02; C07H 1/00; A61K 35/12

[52] U.S. Cl. .............................. 435/2; 435/29; 435/1.3; 536/1.11; 424/520; 424/529; 424/530; 424/531; 424/532; 424/533; 568/862; 530/362; 530/363

[58] Field of Search .............................. 435/2, 240.1, 29, 435/1.3; 424/520, 529, 530, 531, 532, 533; 536/1.11; 568/862; 530/362, 363

[56] References Cited

U.S. PATENT DOCUMENTS

| | | | |
|---|---|---|---|
| 4,764,463 | 8/1988 | Mason et al. | 435/2 |
| 4,980,277 | 12/1990 | Junnila | 435/2 |
| 5,160,312 | 11/1992 | Voelkel | 600/34 |
| 5,328,821 | 7/1994 | Fisher et al. | 435/2 |
| 5,364,756 | 11/1994 | Livesey et al. | 435/2 |

FOREIGN PATENT DOCUMENTS 9103935   4/1991   WIPO.

OTHER PUBLICATIONS

Valeri, C. R., "Transfusion", vol. 15, No. 3, pp. 195-218, 1975. Month not available.

Yamashita, T., "Cryobiology", vol. 17, pp. 112-119, 1980. Month not available.

*Primary Examiner*—Louise Leary
*Attorney, Agent, or Firm*—Michael S. Sherrill

[57] ABSTRACT

A simple, inexpensive, physiologically compatible, cryopreservation solution which includes the innocuous components of (i) glycerol, (ii) an alkali metal chloride salt, (iii) a monosaccharide, and (iv) serum albumin.

21 Claims, No Drawings

CRYOPRESERVATION SOLUTION

This is a continuation of U.S. patent application Ser. No. 08/399,077, filed 08 Mar. 1995 now U.S. Pat. No. 5,580,714.

FIELD OF THE INVENTION

This invention relates to cryopreservation solutions. More specifically, this invention is directed to cryopreservation solutions which are particularly suited for use in cryopreserving the various types of cells circulating in blood or found in bone marrow such as hematopoietic stem and progenitor cells.

This invention also relates to methods for cryopreserving and recovering cryopreserved cells.

BACKGROUND OF THE INVENTION

Blood

The morphologically recognizable and functionally capable cells circulating in blood include erythrocytes, neutrophilic, eosinophilic, and basophilic granulocytes, B-lymphocytes, T-lymphocytes, nonB-lymphocytes, nonT-lymphocytes, and platelets. These mature cells derive from and are replaced, on demand, by morphologically recognizable dividing precursor cells for the respective lineages such as erythroblasts for the erythrocyte series, myeloblasts, promyelocytes and myelocytes for the granulocyte series, and megakaryocytes for the platelets.

Hematopoietic Stem and Progenitor Cells

The precursor cells derive from more primitive cells that can simplistically be divided into two major subgroups: stem cells and progenitor cells. The definitions of stem and progenitor cells are operational and depend on functional rather than on morphological criteria. Stem cells have extensive self-renewal or self-maintenance capacity. Some of the stem cells differentiate upon need, but some stem cells or their daughter cells produce other stem cells to maintain the precious pool of these cells. Thus, in addition to maintaining their own kind, pluripotential stem cells are capable of differentiation into several sublines of progenitor cells with more limited self-renewal capacity or no self-renewal capacity. These progenitor cells ultimately give rise to the morphologically recognizable precursor cells. The progenitor cells are capable of proliferating and differentiating along one, or more than one, of the myeloid differentiation pathways.

Stem and progenitor cells make up a very small percentage of the nucleated cells in the bone marrow, spleen, and blood. About ten times fewer of these cells are present in the spleen relative to the bone marrow, with even less present in the adult blood. As an example, approximately one in one thousand nucleated bone marrow cells is a progenitor cell; stem cells occur at a lower frequency.

Reconstitution of the hematopoietic system has been accomplished by bone marrow transplantation. Lorenz and coworkers showed that mice could be protected against lethal irradiation by intravenous infusion of bone marrow (Lorenz, 20 E., et al., 1951, J. Natl. Cancer Inst. 12:197–201). Later research demonstrated that the protection resulted from colonization of recipient bone marrow by the infused cells (Lindsley, D. L., et al., 1955, Proc. Soc. Exp. Biol. Med. 90:512–515; Nowell, P. C., et al., 1956, Cancer Res. 16:258–261; Mitchison, N. A., 1956, Br. J. Exp. Pathol. 37:239–247; Thomas, E. D., et al., 1957, N. Engl. J. Med. 257:491–496). Thus, stem and progenitor cells in donated bone marrow can multiply and replace the blood cells responsible for protective immunity, tissue repair, clotting, and other functions of the blood. In a successful bone marrow transplantation, the blood, bone marrow, spleen, thymus and other organs of immunity are repopulated with cells derived from the donor.

Bone marrow has been used with increasing success to treat various fatal or crippling diseases, including certain types of anemias such as aplastic anemia (Thomas, E. D., et al., Feb. 5, 1972, The Lancet, pp. 284–289), Fanconi's anemia (Gluckman, E., et al., 1980, Brit J. Haematol. 45:557–564; Gluckman, E., et al., 1983, Brit J. Haematol. 54:431–440; Gluckman, E., et al., 1984, Seminars in Hematology:21 (1):20–26), immune deficiencies (Good, R. A., et al., 1985, Cellular Immunol. 82:36–54), cancers such as lymphomas or leukemias (Cahn, J. Y., et al., 1986, Brit. J. Haematol. 63:457–470; Blume, K. J. and Forman S. J., 1982, J. Cell. Physiol. Supp. 1:99–102; Cheever, M. A., et al., 1982, N. Engl. J. Med. 307(8):479–481), carcinomas (Blijham, G., et al., 1981, Eur. J. Cancer 17(4):433–441), various solid tumors (Ekert, H., et al., 1982, Cancer 49:603–609; Spitzer, G., et al., 1980, Cancer 45:3075–3085), and genetic disorders of hematopoiesis.

Bone marrow transplantation has also recently been applied to the treatment of inherited storage diseases (Hobbs, J. R., 1981, Lancet 2:735–739), thalassemia major (Thomas, E. D., et al., 1982, Lancet 2:227–229), sickle cell disease (Johnson, F. J., et al., 1984, N. Engl. J. Med. 311:780–783), and osteopetrosis (Coccia, P. F., et al., 1980, N. Engl. J. Med. 302:701–708) (for general discussions, see Storb, R. and Thomas, E. D., 1983, Immunol. Rev. 71:77–102; O'Reilly, R., et al., 1984, Sem. Hematol. 21(3):188–221; 1969, Bone-Marrow Conservation, Culture and Transplantation, Proceedings of a Panel, Moscow, Jul. 22–26, 1968, International Atomic Energy Agency, Vienna; McGlave, P. B., et al., 1985, in Recent Advances in Haematology, Hoffbrand, A. V., ed., Churchill Livingstone, London, pp. 171–197).

Present use of bone marrow transplantation is severely restricted, since it is extremely rare to have perfectly matched (genetically identical) donors, except in cases where an identical twin is available or where bone marrow cells of a patient in remission are stored in a viable frozen state. Even in such an autologous system, the danger due to undetectable contamination with malignant cells, and the necessity of having a patient healthy enough to undergo marrow procurement, present serious limitations. Except in such autologous cases, there is an inevitable genetic mismatch of some degree, which entails serious and sometimes lethal complications. These complications are two-fold. First, the patient is usually immunologically incapacitated by drugs beforehand, in order to avoid immune rejection of the foreign bone marrow cells (host versus graft reaction). Second, when and if the donated bone marrow cells become established, they can attack the patient (graft versus host disease), who is recognized as foreign. Even with closely matched family donors, these complications of partial mismatching are the cause of substantial mortality and morbidity directly due to bone marrow transplantation from a genetically different individual.

Peripheral blood has also been investigated as a source of stem cells for hematopoietic reconstitution (Nothdurtt, W., et al., 1977, Scand. J. Haematol. 19:470–471; Sarpel, S. C., et al., 1979, Exp. Hematol. 7:113–120; Ragharachar, A., et al., 1983, J. Cell. Biochem. Suppl. 7A:78; Juttner, C. A., et al., 1985, Brit. J. Haematol. 61:739–745; Abrams, R. A., et al., 1983, J. Cell. Biochem. Suppl. 7A:53; Prummer, O., et al., 1985, Exp. Hematol. 13:891–898). In some studies, promising results have been obtained for patients with various leukemias (Reiffers, J., et al., 1986, Exp. Hematol.

14:312–315 (using cryopreserved cells); Goldman, J. M., et al., 1980, Br. J. Haematol. 45:223–231; Tilly, H., et al., Jul. 19, 1986, The Lancet, pp. 154–155; see also To, L. B. and Juttner, C. A., 1987, Brit. J. Haematol. 66:285–288, and references cited therein); and with lymphoma (Korbling, M., et al., 1986, Blood 67:529–532). It has been implied that the ability of autologous peripheral adult blood to reconstitute the hematopoietic system, seen in some cancer patients, is associated with the far greater numbers of circulating progenitor cells in the peripheral blood produced after cytoreduction due to intensive chemotherapy and/or irradiation (the rebound phenomenon) (To, L. B. and Juttner, C. A., 1987, Annot., Brit. J. Haematol. 66:285–288; see also 1987, Brit. J. Haematol. 67:252–0253, and references cited therein). Other studies using peripheral blood have failed to effect reconstitution (Hershko, C., et al., 1979, The Lancet 1:945–947; Ochs, H. D., et al., 1981, Pediatr. Res. 15(4 Part 2):601).

Studies have also investigated the use of fetal liver cell transplantation (Cain, G. R., et al., 1986, Transplantation 41(1):32–25; Ochs, H. D., et al., 1981, Pediatr. Res. 15(4 part 2):601; Paige, C. J., et al., 1981, J. Exp. Med. 153:154–165; Touraine, J. L., 1980, Excerpta Med. 514:277; Touraine, J. L., 1983, Birth Defects 19:139; see also Good, R. A., et al., 1983, Cellular Immunol. 82:44–45 and references cited therein) or neonatal spleen cell transplantation (Yunis, E. J., et al., 1974, Proc. Natl. Acad. Sci. U.S.A. 72:4100) as stem cell sources for hematopoietic reconstitution. Cells of neonatal thymus have also been transplanted in immune reconstitution experiments (Vickery, A. C., et al., 1983, J. Parasitol. 69(3):478–485; Hirokawa, K., et al., 1982, Clin. Immunol. Immunopathol. 22:297–304).

Cryopreservation Solutions and Techniques

Freezing has long been used to preserve living cells, such as blood cells, after they have been removed or separated from a donating organism. The cryopreservation and recovery of living cells, however, has proven to be quite troublesome. Cells are subjected to relatively harsh conditions during both the freezing and thawing cycles involved in the cryopreservation of cells, resulting in a low survivability rate.

Freezing is destructive to most living cells. As the external medium freezes cells attempt to maintain equilibrium and lose water, thus increasing intracellular solute concentration, until intracellular freezing occurs at about minus 10°–15° C. It is generally believed that both intracellular freezing and solution effects are responsible for cell injury. For example, it has been proposed that freezing destruction from extracellular ice is essentially a plasma membrane injury resulting from osmotic dehydration of the cell.

Substantial time and effort has been expended in an effort to maximize the viability of thawed cells. Such efforts have generally focused upon the development of cryoprotective agents and establishing optimal cooling rates.

Cryoprotection by solute addition is thought to occur by two potential mechanisms: (i) intracellular; by reducing the amount of ice formed within the cell; and/or (ii) extracellular; by decreasing water flow out of the cell in response to a decreased vapor pressure caused by the formation of ice in the solute surrounding the cells.

Different optimal cooling rates have been described for different cells. Various groups have looked at the effect of cooling velocity or cryopreservatives upon the survival or transplantation efficiency of frozen bone marrow cells and red blood cells (Lovelock, J. E. and Bishop, M. W. H., 1959, Nature 183:1394–1395; Ashwood-Smith, M. J., 1961, Nature 190:1204–1205; Rowe, A. W. and Rinfret, A. P., 1962, Blood 20:636; Rowe, A. W., and Fellig, J., 1962, Fed. Proc. 21:157; Rowe, A. W., 1966, Cryobiology 3(1):12–18; Lewis, J. P., et al., 1967, Transfusion 7(1):17–32; Rapatz, G., et al., 1968, Cryobiology 5(1):18–25; MaZur, p., 1970, Science 168:939–949; Mazur, P., 1977, Cryobiology 14:251–272; Rowe, A. W. and Lenny, L. L., 1983, Cryobiology 20:717; Stiff, P. J., et al., 1983, Cryobiology 20:17–24; Gorin, N. C., 1986, Clinics in Haematology 15(1):19–48). Generally, optimal results for the freezing of hematopoietic stem and progenitor cells can be achieved with a cooling rate of about 1°–2° C. per minute with a final storage temperature of about −70° to about −196° C. with other blood cells generally within these same ranges.

The successful recovery of human bone marrow cells after long-term storage in liquid nitrogen has been described (1983, American Type Culture Collection, Quarterly Newsletter 3(4):1). In addition, stem cells in bone marrow were shown capable of withstanding cryopreservation and thawing (Fabian, L., et al., 1982, Exp. Hematol. 10(1):119–122).

The widely accepted industry standard cryoprotectant for use in the cryopreservation of most cells, including whole blood, umbilical cord blood, bone marrow, granulocytes, neutrophils, platelets and hematopoietic stem and progenitor cells, is dimethyl sulfoxide (DMSO). This can generally be attributed to the widespread experience and knowledge of DMSO-based cryopreservation solutions and a general perception that DMSO provides superior protection and maximal cell viability. While DMSO is generally effective for these purposes, it is also known to be physiologically pernicious, particularly at higher concentrations, and thereby tends to irritate both those involved in the cryopreservation process and the patient into whom the cryopreserved cells are introduced with resultant hypertension, vomiting and nausea. The pernicious nature of DMSO is also thought to result in a lower in vitro viability of the cryopreserved cells.

Accordingly, a substantial need exists for a simple, physiologically compatible, alternative cryopreserving solution capable of providing a comparable level of cell viability both in vivo and in vitro.

SUMMARY OF THE INVENTION

I have developed a simple, inexpensive, physiologically compatible, cryopreservation solution which includes the innocuous components of (i) glycerol, (ii) an alkali metal chloride salt, (iii) a monosaccharide, and (iv) serum albumin.

The major constituent of the cryopreservation solution is the cryopreserving agent glycerol (also referenced as glycerin). The alkali metal chloride promotes cell viability through the freeze-thaw cycle. The monosaccharide functions as a nutritional carbon source for the cells. The serum albumin functions as a protein source which provides a coating around the membrane of the target cell so as to protect the membrane during the freeze-thaw cycle and storage of the frozen cells. The serum albumin is also believed to function as a scavenger of oxygen free radicals which are known to adversely impact the viability of various target cells such as the erythrocyte, neutrophilic, eosinophilic, and basophilic granulocytes, B-lymphocytes, T-lymphocytes, nonB-lymphocytes, nonT-lymphocytes, and platelet cells mentioned previously. The source of the serum albumin is preferably matched with the species of the intended subject into which the protected target cells will be introduced.

The cryopreservation solution may be provided in either concentrated or fully diluted form. The concentrated form may be diluted to use strength by simply adding a diluent, such as water which has been suitably treated for injection, into the solution. The diluent is preferably an physiologically balanced salt solution such as saline.

Use of the cryopreservation solution in the preservation and subsequent therapeutic use of target cells, such as whole blood, umbilical cord blood, bone marrow, granulocytes, neutrophils, platelets, and hematopoietic stem and progenitor cells including those identified as CD 34+cells, includes the steps of (i) diluting the concentrated cryopreservation solution as necessary, (ii) introducing the target cells into the diluted solution, (iii) freezing the protected target cells, (iv) thawing the frozen solution to ambient conditions, and (v) introducing the thawed target cells into a subject in need of such target cells. The thawed target cells and accompanying cryopreservation solution is preferably warmed to body temperature (i.e., about 37° C.) prior to introduction into the subject. The physiological compatibility of the cryoprotection solution allows the thawed target cells to be introduced into the subject without separation of the target cells and the cryopreservation solution.

DETAILED DESCRIPTION OF THE INVENTION INCLUDING A BEST MODE

I have discovered a simple, inexpensive, physiologically compatible, cryopreservation solution which consists essentially of (i) glycerol, (ii) an alkali metal chloride salt, (iii) a monosaccharide, and (iv) serum albumin.

As utilized herein, excluding the claims, "wt%", when used in connection with the constituents of the cryopreservation solution, is based upon the total weight of the concentrated cryopreservation solution unless otherwise stated.

Glycerol ($C_3H_8O_3$) is a polyol which is commercially available in U.S.P. and food grade from a number of suppliers including J. T. Baker.

The concentrated cryopreservation solution includes about 60 to about 80 wt% glycerol. Concentrations of less than about 60 wt% glycerol result in reduced cell viability while solutions containing greater than about 80 wt% glycerol result in a solution with an unacceptably high osmolality (i.e., greater than about 2,000 mOsm/kg).

Alkali metal chloride salts suitable for use in this invention include sodium chloride and potassium chloride. The alkali metal chloride salt is believed to promote cell viability through the freeze-thaw cycle by adjusting the osmolality of the cryopreservation solution between about 500 and 2,000 mOsm/kg as measured with a Wescor 5500 Model Vapor Pressure Osmometer in accordance with the protocol provided in the instruction/service manual for the instrument. By way of referenced, the physiological osmolality of blood is generally within the range of about 260 to 320 mOsm/kg. The optimum osmolality within this general range depends upon several factors including the particular target cells, the specific constitution of the cryopreservation solution and the freeze-thaw rate. By way of example, an osmolality about 700 to about 1,700 is generally desired for the cryopreservation of hematopoietic stem and progenitor cells.

The concentrated cryopreservation solution includes about 5 to about 10 wt% alkali metal chloride salt. Concentrations of less than about 5 wt% and greater than about 10 wt% alkali metal chloride salt result in reduced cell viability through the freeze-thaw cycle with concentrations of greater than 10 wt% also susceptible to damaging crystallization.

The monosaccharide, such as glucose, functions as a nutritional carbon source for the cells. Availability of the monosaccharide promotes cell preservation through the freeze-thaw cycle and storage of the frozen cells by ensuring the presence of sufficient nutrients within the cell.

The serum albumin functions as a protein source which provides a coating around the membrane of the target cell so as to protect the membrane during the freeze-thaw cycle and storage of the frozen cells. The serum albumin is also believed to function as a scavenger of oxygen free radicals which are known to adversely impact the viability of various target cells such as the erythrocyte, neutrophilic, eosinophilic, and basophilic granulocytes, B-lymphocytes, T-lymphocytes, nonB-lymphocytes, nonT-lymphocytes, and platelet cells mentioned previously. The source of the serum albumin is preferably matched with the species of the intended subject into which the protected target cells will be introduced.

Effective concentrations can be attained by incorporation of about 0.2 to about 1 wt% monosaccharide in the concentrated cryopreservation solution. A loading of less than about 0.2 wt% provides an insufficient concentration and reduces cell viability through the freeze-thaw cycle while concentrations greater than about 1 wt% do not provide a proportional increase in cell viability and adversely impact the concentrations of the other constituents. The serum albumin functions as a protein source which provides a coating around the membrane of the target cell so as to protect the membrane during the freeze-thaw cycle and storage of the frozen cells.

Effective concentrations can be attained by incorporation of about 20 to about 30 wt% serum albumin. A concentration of less than about 20 wt% serum albumin provides an insufficient concentration and results in reduced cell viability while concentrations greater than about 30 wt% do not provide a proportional increase in cell viability and tend to increase the osmolality of the solution above the desired upper limit of about 2,000 mOsm/kg.

The concentrated cryopreservation solution can be diluted to use concentration by the addition of a suitable diluent (e.g., 0.9 wt% saline from ultrafiltered water, water for injection, and autologous plasma) at a ratio of from about 1 to 10 parts, typically 1 to 2 parts, diluent to 1 part concentrated cryopreservation solution. Generally, the diluted cryopreservation solution will consist essentially of (i) about 20 to about 40 wt% glycerol, (ii) about 1.5 to about 5 wt% alkali metal chloride salt, (iii) about 0.1 to about 0.5 wt% monosaccharide, and (iv) about 6 to about 15 wt% serum albumin, based upon the diluted cryopreservation solution. The balance is diluent.

The cryopreservation solution should be formulated to provide a pH of between about 7 and 7.5.

Target cells may be conveniently cryopreserved using the diluted cryopreservation solution by simply (i) introducing the target cells into the diluted cryopreservation solution, and (ii) freezing or cryopreserving the protected target cells. The volume of diluted cryopreservation solution which should be added to the target cells depends upon both the volumetric ratio of target cell containing solution to cryopreservation solution and the ratio of target cell to cryopreservation solution. The volumetric ratio of target cell containing solution to cryopreservation solution should generally be between about 1:1 to 1:10 with the ratio of target cells to cryopreservation solution between about $1\times10^5$ cells/ml to about $1:1\times10^9$ cells/ml with a generally preferred ratio of between about $2\times10^8$ cells/ml to $3\times10^8$ cells/ml. Ratios of greater than those set forth above tend to result in a decrease in the concentration of viable cells due to insufficient cryopreservation solution, while ratios less than those set forth above simply result in an inefficient use of the cryopreservation solution and the need to introduce excessive cryopreservation solution into a subject in order to introduce effective amounts of the target cells. Target cells are often available for preservation only in dilute form as a constituent in a biological fluid (e.g., stem cells concentrated from peripheral blood commonly contain stem cells at a concentration of about $1\times10^6$ cells/ml to about $3\times10^8$ cells/ml with the balance comprising other blood components such as plasma and platelets). These biologically diluted samples must generally be combined with the cryopreservation solution at a volumetric ratio of about 2:1 to 1:4 (depending of course upon a number of factors including the specific formulation of the diluted cryopreservation solution, the concentration of target cells in the biologically diluted sample, the type of target cells, etc.) to achieve the optimum ratio of target cells to cryopreservation solution. The final, target cell containing solution, should generally contain about 4 to 12 wt% glycerol and about 2 to 10 wt% albumin, with variations outside of this general range contemplated for certain applications.

Cryopreserved protected target cells must be thawed prior to introduction of the target cells into a subject. Thanks to the physiological compatibility of the cryoprotection solution, the thawed target cells may to be introduced into the subject without separating the target cells and the cryopreservation solution. The thawed target cells may be maintained for several hours at room temperature without an appreciable loss in cell viability. The thawed solution may be slowly diluted with saline or other appropriate ionic solution to so as to reduce the osmolality of the solution from the desired cryopreservation range of 500 to 2,000 mOsm/kg down to the physiological range of 260 to 320 mOsm/kg so as to reduce shock to the cell walls caused by sudden changes in osmolality.

A controlled slow cooling rate is can often be effective for achieving optimal cell viability. It is generally believed that different cell types have different optimal cooling rates (See, e.g. Rowe, A. W. and Rinfret, A. P., 1962, Blood 20:636; RoWe, A. W., 1966, Cryo Biology 3(1):12–18; Lewis, J. P., et al., 1967, transfusion 7(1):17–32; and Mazur, P., 1970 Science 168:939–949 for effects of cooling velocity on survival of marrow-stem cells and on their transplantation potential).

The cryopreservation solution can be maintained at room temperature prior to use and the blended target cells held at room temperature for as long as thirty minutes before freezing is commenced without an appreciable loss in cell viability. This is in contrast to the toxic cryoprotectant DMSO which must be cooled to about 4° C. prior to the addition of target cells in order to expedite the freezing process and requires that the freezing process commence immediately after the DMSO is added to the cells in order to minimize cell death induced by the presence of DMSO.

Controlled freezing can be carried out by use of a programmable freezing device. Programmable freezing apparatuses allow determination of optimal cooling rates and facilitate standard reproducible cooling.

The container holding the cells must be stable at cryogenic temperatures and allow for rapid heat transfer for effective control of both freezing and thawing. Sealed plastic vials (e.g., Nunc and Wheaton cryules) or glass ampules can be used for multiple small amounts (1 to 2 ml), while larger volumes of 100 to 200 ml can be frozen in polyolefin bags, such as those available from Fenwal, held between metal plates.

The frozen cells can then be transferred to a long-term cryogenic storage vessel. In a preferred embodiment samples can be cryogenically stored in liquid nitrogen (−196° C.) or liquid nitrogen vapor (−105° C.). Such storage is greatly facilitated by the availability of highly efficient liquid nitrogen refrigerators.

When needed, the frozen cells are preferably thawed quickly and maintained at about 37° C. until used. Since the cryoprotective solution is physiologically compatible, it need not be removed prior to introduction into the subject.

Cryopreserved and thawed umbilical cord cells, platelets, and hematopoietic stem and progenitor cells can be used therapeutically for reconstitution of the hematopoietic system in a suitable patient. The cells can be introduced by any method known in the art with systemic infusion generally preferred.

Reconstitution of the hematopoietic system (or immune system) can be therapeutically valuable for a large number of diseases and disorders. The infusion of cyropreserved hematopoietic stem and progenitor cells for hematopoietic reconstitution can be beneficially used in the treatment of those diseases which are presently known to be curable by autogeneic bone marrow transplantation.

Disorders that can be treated by infusion of stem cells include, but are not limited to, five broad categories. First are diseases resulting from a failure or dysfunction of normal blood cell production and maturation (i.e., aplastic anemia and hypoproliferative stem cell disorders). The second group includes neoplastic malignant diseases in the hematopoietic organs (e.g., leukemia and lymphomas). The third group of disorders comprises those patients with a broad spectrum of malignant solid tumors of nonhematopoietic origin. Stem cell infusion in these patients serves as a bone marrow rescue procedure, which is provided to a patient following otherwise lethal chemotherapy or irradiation of the malignant tumor. The fourth group of diseases consists of autoimmune conditions, where the stem cells serve as a source of replacement of an abnormal immune system. The fifth group of diseases comprises a number of genetic disorders which can be corrected by infusion of hematopoietic stem cells, preferably syngeneic, which prior to transplantation have undergone gene therapy.

I claim:

1. A concentrated cryopreservation solution, consisting essentially of:
   (a) glycerol;
   (b) an alkali metal chloride salt in an amount effective for promoting cell viability;
   (c) a biologically metabolizable monosaccharide in an amount effective for supporting cell maintenance under ambient conditions; and
   (d) serum albumin in an amount effective for supporting plasma membrane integrity;
   (e) wherein the pH of the solution is between about 7 and 7.5.

2. The cryopreservation solution of claim 1 further including a diluent.

3. The concentrated cryopreservation solution of claim 1 wherein the alkali metal chloride salt is sodium chloride.

4. The concentrated cryopreservation solution of claim 1 wherein the monosaccharide is glucose.

5. The concentrated cryopreservation solution of claim 1 wherein the serum albumin is human serum albumin.

6. A method of cryopreserving cells, comprising (i) introducing target cells into the cryopreservation solution of claim 2, and (ii) cryopreserving the protected target cells.

7. The method of claim 6 wherein the volumetric ratio of target cell containing solution to cryopreservation solution is between about 1:1 to 1:10 and the ratio of target cells to cryopreservation solution is between about $1\times10^5$ cells/ml to about $1\times10^9$ cells/ml.

8. The method of claim 6 wherein the target cells are hematopoietic stem or progenitor cells.

9. The method of claim 6 wherein the target cells are blood platelet cells.

10. The method of claim 6 wherein the target cells are cells identified as CD 34+cells.

11. The method of claim 6 wherein the target cells are obtained from umbilical cord blood.

12. A method for cryopreserving and recovering viable cells, comprising (i) introducing target cells into the cryopreservation solution of claim 2, (ii) cryopreserving the protected target cells, and (iii) thawing the protected target cells.

13. The method of claim 12 wherein the volumetric ratio of target cell containing solution to cryopreservation solution is between about 1:1 to 1:10 and the ratio of target cells to cryopreservation solution is between about $1\times10^5$ cells/ml to about $1\times10^9$ cells/ml.

14. The method of claim 12 wherein the target cells are hematopoietic stem or progenitor cells.

15. A method for the cryopreservation, recovery and therapeutic use of cells, comprising (i) introducing target cells into the cryopreservation solution of claim 2, (ii) cryopreserving the protected target cells, (iii) thawing the protected target cells, and (iv) introducing the thawed protected target cells into a subject in need of such target cells without separation of the target cells and the cryopreservation solution.

16. The method of claim 15 wherein the volumetric ratio of target cell containing solution to cryopreservation solution is between about 1:1 to 1:10 and the ratio of target cells to cryopreservation solution is between about $1\times10^5$ cells/ml to about $1\times10^9$ cells/ml.

17. The method of claim 15 wherein the target cells are hematopoietic stem or progenitor cells.

18. The method of claim 15 wherein the target cells are blood platelet cells.

19. The method of claim 15 wherein the target cells are cells identified as CD 34+cells.

20. The method of claim 15 wherein the target cells are obtained from umbilical cord blood.

21. The method of claim 15 wherein the subject is a human.

* * * * *